United States Patent
Saito et al.

(10) Patent No.: US 7,084,306 B2
(45) Date of Patent: Aug. 1, 2006

(54) PROCESS FOR PREPARING β-DIKETONE COMPOUND AND PROCESS FOR PREPARING METAL COMPLEX THEREOF

(75) Inventors: Makoto Saito, Kanagawa (JP); Takashi Ueda, Kanagawa (JP); Takashi Tani, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 33 days.

(21) Appl. No.: 10/500,963

(22) PCT Filed: Dec. 18, 2002

(86) PCT No.: PCT/JP02/13238

§ 371 (c)(1),
(2), (4) Date: Jul. 8, 2004

(87) PCT Pub. No.: WO03/059858

PCT Pub. Date: Jul. 24, 2003

(65) Prior Publication Data

US 2005/0119466 A1 Jun. 2, 2005

Related U.S. Application Data

(60) Provisional application No. 60/384,393, filed on Jun. 3, 2002.

(30) Foreign Application Priority Data

Jan. 9, 2002 (JP) ............................. 2002-002727
May 27, 2002 (JP) ............................. 2002-151760

(51) Int. Cl.
C07C 45/72 (2006.01)
C07C 11/00 (2006.01)
C07F 9/00 (2006.01)
C07F 7/00 (2006.01)

(52) U.S. Cl. ...................... 568/385; 568/388; 568/391; 556/41; 556/42; 556/51; 556/57

(58) Field of Classification Search ................ 568/385, 568/388, 391; 556/41, 42, 51, 57
See application file for complete search history.

(56) References Cited

U.S. PATENT DOCUMENTS 5,344,992 A * 9/1994 Drewes et al. ............... 568/388
6,143,935 A * 11/2000 Boaz et al. .................. 568/314

FOREIGN PATENT DOCUMENTS

EP 454624 A 10/1991

OTHER PUBLICATIONS

Swaelens, G. et al: "NMR experiments on acetals. XXVI. Influence of β-substitution on geminal coupling values in 1,3-dioxanes"0 Bulletin Des Societes Chimiques Belges (1970), 79(7-8), 441-50, p. 448, XP000983130.
Chemical Abstracts, vol. 116, No. 19, May 11, 1992 Columbus, Ohio, US; abstract No. 193677WU, Yuehuan et al, "Synthesis of 2,2,6,6-tetramethylheptane-3,5-dione (dipivaloylmethane)" XP002248216 abstract & Huaxue Shiji (1991), 13(6), 379, 372.
Chemical Abstracts, vol. 126, No. 7, Feb. 17, 1997 Columbus, Ohio, US; abstract No. 98457 Rees, William S. , Jr. et al: "Tris (2,2,6,6-tetramethyl-3 , 5-heptanedionato) yttrium" XP00248217 abstract & Inorganic Syntheses (1997) , 31, 302-306.
Database WPI Section Ch, Week 200255 Derwent Publications Ltd., London, GB; Class E12, AN 1994-124127, XP002248218 & JP 03 307685 B (Nippon Sanso KK), Jul. 24, 2002 abstract.
Patent Abstracts of Japan vol. 18, No. 30 (C-1153), Jan. 17, 1994, abstract of JP 05 255855A of Oct. 5, 1993.
Joe T. Adams and Charles R. Hauser; The Acylation of Methyl Ketones with Aliphatic Esters by Means of Sodium Amide. Synthesis of β-Diketones of the Type ROCH$_2$COR[1]; J. Am. Chemical Society, vol. 66, pp. 1220-1222(1944).
Karl R. Kopecky, Derek Nonhebel, Gene Morris, and George S. Hammond; Preparation of Dipivaloylmethane, J. Org. Chemical, vol. 27, pp. 1036-1037 (1962).
Kent J. Eisentraut and Robert E. Sievers; Volatile Rare-Earth Chelates of 2,2,6,6-Tetramethylheptane-3,5-Dione, Inorganic Synthesis, 11, pp. 94-98 (1968).
William S. Rees, Jr. and Michael W. Carris; Bis(2,2,6,6-Tetramethyl-3,5-Heptanedionato) Copper, Inorganic Synthsis, 31, pp. 286-288 (1997).

* cited by examiner

*Primary Examiner*—Sikarl A. Witherspoon
(74) *Attorney, Agent, or Firm*—Sughrue Mion, PLLC

(57) ABSTRACT

Disclosed is a process for preparing 2,2,6,6-tetramethyl-3,5-heptanedione, comprising reacting a pivalic acid alkyl ester with pinacolone in the presence of an alkali metal alkoxide catalyst using a pivalic acid alkyl ester as a solvent but using no other solvent or reacting them in an amide type or urea type solvent in the presence of an alkali metal alkoxide catalyst. Also disclosed is a process for preparing a 2,2,6,6-tetramethyl-3,5-heptanesione metal complex using the 2,2,6,6-tetramethyl-3,5-heptanedione obtained by the above process. The process for preparing 2,2,6,6-tetramethyl-3,5-heptanedione is an industrially advantageous process in which an alkali metal alkoxide that is easy to handle can be used as a catalyst for preparing 2,2,6,6-tetramethyl-3,5-heptanedione from a pivalic acid alkyl ester and pinacolone.

27 Claims, No Drawings

US 7,084,306 B2

PROCESS FOR PREPARING β-DIKETONE COMPOUND AND PROCESS FOR PREPARING METAL COMPLEX THEREOF

CROSS REFERENCES OF RELATED APPLICATION

This application is the national stage application of PCT/JP02/13238 filed Dec. 18, 2002, and published as WO 03/059858 on Jul. 24, 2003, and claiming benefit pursuant to 35 U.S.C. 119(e) (1) of the filing date of Provisional Application 60/384,393 filed on Jun. 3, 2002 pursuant to 35 U.S.C. 111(b).

FIELD OF THE INVENTION

The present invention relates to a process for preparing a β-diketone compound that is useful as a ligand of a volatile organometallic complex used as, for example, a starting material of MOCVD (metal organic chemical vapor deposition), and more particularly to a process for preparing 2,2,6,6-tetramethyl-3,5-heptanedione.

The present invention also relates to a process for preparing a 2,2,6,6-tetramethyl-3,5-heptanedione metal complex using the 2,2,6,6-tetramethyl-3,5-heptanedione.

BACKGROUND OF THE INVENTION

As a process for the production of inorganic or metal thin films, MOCVD has been widely applied, and as MOCVD materials, metal alkoxides, β-diketone complexes, etc. have been developed. Of these, 2,2,6,6-tetramethyl-3,5-heptanedione is known to form volatile complexes together with relatively many kinds of metals, but this compound has not become so widespread industrially because it is expensive.

A process using Claisen condensation is well known as a process for preparing the 2,2,6,6-tetramethyl-3,5-heptanedione. For example, in J. Am. Chem. Soc., 66, 1220 (1944), ethyl pivalate is reacted with pinacolone (3,3-dimethyl-2-butanone, tert-butyl methyl ketone) using a sodium amide catalyst to synthesize 2,2,6,6-tetramethyl-3,5-heptanedione in a yield of 28%. In this report, acylation reaction of methyl ketone with an ester using sodium ethoxide is also described, and it is reported that the reactivity is inferior when a higher ester is used.

In J. Org. Chem., 27, 1036 (1962), methyl pivalate is reacted with pinacolone using a sodium hydride catalyst to synthesize 2,2,6,6-tetramethyl-3,5-heptanedione in a yield of 60 to 70%.

Other examples of the process for preparing 2,2,6,6-tetramethyl-3,5-heptanedione using Claisen condensation reaction have also been reported. In any of these processes, however, sodium hydride or sodium amide that is difficult to handle similarly to the metallic sodium is used, and there resides a problem of safety. Moreover, safety countermeasures thereto are necessary, and hence, it is difficult to use these processes industrially.

In addition to the above processes, a synthesis process using Grignard reaction of malonyl chloride with t-BuMgCl (t-Bu is a tert-butyl group) and a synthesis process using a reaction of malonyl chloride with t-BuCu(Li)SPh have been reported. In these processes, however, an extremely low temperature of about −70° C. is necessary, and handling is very difficult. Thus, there are problems in the industrial practice.

As described above, any industrially advantageous process wherein 2,2,6,6-tetramethyl-3,5-heptanedione can be prepared by simple and easy operations at a low cost has been unknown so far, and further improvement has been desired.

OBJECT OF THE INVENTION

It is an object of the present invention to provide an industrially advantageous process wherein a β-diketone compound represented by the following formula (3) can be obtained.

$$CR^1R^2R^3COCHR^8COCR^5R^6R^7 \quad (3)$$

wherein $R^1$ to $R^3$ and $R^5$ to $R^7$ are each independently an alkyl group of 1 to 3 carbon atoms, and $R^8$ is hydrogen or an alkyl group of 1 to 4 carbon atoms.

Particularly, it is an object of the present invention to provide an industrially advantageous process wherein 2,2,6,6-tetramethyl-3,5-heptanedione can be obtained easily and at a low cost.

More specifically, it is an object of the invention to provide a process wherein an alkali metal alkoxide catalyst can be used for the reaction of an ester compound represented by the formula (1):

$$CR^1R^2R^3COOR^4 \quad (1)$$

wherein $R^1$ to $R^3$ are each independently an alkyl group of 1 to 3 carbon atoms, and $R^4$ is an alkyl group, with a ketone compound represented by the formula (2):

$$CR^5R^6R^7COCH_2R^8 \quad (2)$$

wherein $R^5$ to $R^7$ are each independently an alkyl group of 1 to 3 carbon atoms, and $R^8$ is hydrogen or an alkyl group of 1 to 4 carbon atoms, to prepare the β-diketone compound represented by the formula (3).

That is to say, it is an object of the invention to provide a process wherein an alkali metal alkoxide can be used as a catalyst for preparing 2,2,6,6-tetramethyl-3,5-heptanedione from a pivalic acid alkyl ester and pinacolone which are starting materials.

It is another object of the invention to provide a process for preparing a 2,2,6,6-tetramethyl-3,5-heptanedione metal complex by reacting the 2,2,6,6-tetramethyl-3,5-heptanedione prepared as above with a metal salt.

The present inventors have earnestly studied to solve such problems associated with the prior art as described above, and as a result, they have found that 2,2,6,6-tetramethyl-3,5-heptanedione can be synthesized in the presence of an alkali metal alkoxide catalyst that is easy to handle by reacting a pivalic acid alkyl ester with pinacolone using a pivalic acid alkyl ester as a solvent but using no other solvent in the beginning of the reaction or by reacting them in an amide type or urea type solvent. Based on the finding, the present invention has been accomplished.

Further, the present inventors have also found that by the reaction of the thus prepared 2,2,6,6-tetramethyl-3,5-heptanedione with a metal salt, a 2,2,6,6-tetramethyl-3,5-heptanedione metal complex can be readily obtained.

SUMMARY OF THE INVENTION

That is to say, the present invention is as follows.

[1] A process for preparing a β-diketone compound represented by the following formula (3), comprising a step 1 of reacting an ester compound represented by the following formula (1) with a ketone compound represented by the following formula (2) in the presence of an alkali metal alkoxide catalyst, $$CR^1R^2R^3COOR^4 \quad (1)$$

wherein $R^1$ to $R^3$ are each independently an alkyl group of 1 to 3 carbon atoms, and $R^4$ is an alkyl group, $$CR^5R^6R^7COCH_2R^8 \quad (2)$$

wherein $R^5$ to $R^7$ are each independently an alkyl group of 1 to 3 carbon atoms, and $R^8$ is hydrogen or an alkyl group of 1 to 4 carbon atoms, $$CR^1R^2R^3COCHR^8COCR^5R^6R^7 \quad (3)$$

wherein $R^1$ to $R^3$ and $R^5$ to $R^8$ have the same meanings as defined above.

[2] The process for preparing a β-diketone compound according to the process as described in [1], wherein at least one compound selected from an ester compound represented by the following formula (1), an amide type solvent and a urea type solvent is used as a solvent, $$CR^1R^2R^3COOR^4 \quad (1)$$

wherein $R^1$ to $R^3$ are each independently an alkyl group of 1 to 3 carbon atoms, and $R^4$ is an alkyl group.

[3] The process for preparing 2,2,6,6-tetramethyl-3,5-heptanedione according to the process as described in [1], wherein the compound represented by the formula (1) is a pivalic acid alkyl ester wherein $R^1$ to $R^3$ are each a methyl group, the compound represented by the formula (2) is pinacolone wherein $R^5$ to $R^7$ are each a methyl group and $R^8$ is hydrogen, and the compound represented by the formula (3) is 2,2,6,6-tetramethyl-3,5-heptanedione wherein $R^1$ to $R^3$ and $R^5$ to $R^7$ are each a methyl group and $R^8$ is hydrogen.

[4] The process for preparing 2,2,6,6-tetramethyl-3,5-heptanedione according to the process as described in [3], wherein the reaction is carried out using a pivalic acid alkyl ester as a solvent and using no other solvent.

[5] The process for preparing 2,2,6,6-tetramethyl-3,5-heptanedione according to the process as described in [3], wherein an amide type solvent or a urea type solvent is used as a solvent.

[6] The process for preparing 2,2,6,6-tetramethyl-3,5-heptanedione according to the process as described in [5], wherein the solvent is at least one solvent selected from N,N-dimethylformamide, N,N-dimethylacetamide, N-methylpyrrolidone and 1,3-dimethyl-2-imdazolidinone.

[7] The process for preparing 2,2,6,6-tetramethyl-3,5-heptanedione according to the process as described in [6], wherein the solvent is N,N-dimethylformamide and/or 1,3-dimethyl-2-imidazolidinone.

[8] The process for preparing 2,2,6,6-tetramethyl-3,5-heptanedione according to the process as described in [4], wherein the amount of the solvent used is in the range of 3 to 30 times by mass based on the pinacolone.

[9] The process for preparing 2,2,6,6-tetramethyl-3,5-heptanedione according to the process as described in [3], wherein the alkali metal of the alkali metal alkoxide catalyst is sodium or potassium.

[10] The process for preparing 2,2,6,6-tetramethyl-3,5-heptanedione according to the process as described in [9], wherein the alcohol portion of the alkali metal alkoxide catalyst is a tertiary alcohol.

[11] The process for preparing 2,2,6,6-tetramethyl-3,5-heptanedione according to any one of the processes as described in [3], wherein the amount of the alkali metal alkoxide catalyst used is in the range of 1 to 10 times by mol based on the pinacolone.

[12] A process for preparing 2,2,6,6-tetramethyl-3,5-heptanedione, comprising the step 1 of any one of the processes as described in [3] to [11] to synthesize 2,2,6,6-tetramethyl-3,5-heptanedione by reacting the pivalic acid alkyl ester with the pinacolone in the presence of the alkali metal alkoxide catalyst and a step 2 of adding an acid to the reaction solution of 2,2,6,6-tetramethyl-3,5-heptanedione to perform neutralization and adding water to the solution to separate the solution into two layers and thereby isolate the 2,2,6,6-tetramethyl-3,5-heptanedione as an oil layer.

[13] The process for preparing 2,2,6,6-tetramethyl-3,5-heptanedione according to the process as described in [12], wherein the acid is at least one acid selected from sulfuric acid, hydrochloric acid and nitric acid.

[14] A process for preparing 2,2,6,6-tetramethyl-3,5-heptanedione, comprising recovering a pivalic acid alkyl ester, pinacolone and a solvent from the oil layer containing 2,2,6,6-tetramethyl-3,5-heptanedione obtained in the process as described in [12] or [13] by distillation separation and reusing them in the reaction.

[15] A process for preparing a 2,2,6,6-tetramethyl-3,5-heptanedione metal complex, comprising a step 3 of reacting the 2,2,6,6-tetramethyl-3,5-heptanedione obtained in any one of the processes as described in [3] to [14] with a metal salt.

The process for preparing a 2,2,6,6-tetramethyl-3,5-heptanedione metal complex according to the process as described in [15], wherein the metal salt is at least one metal salt selected from the group consisting of a halide, a nitrate, a sulfate and a phosphate of a metal.

[17] The process for preparing a 2,2,6,6-tetramethyl-3,5-heptanedione metal complex according to the process as described in [16], wherein the metal salt is a chloride of a metal and/or a nitrate of a metal.

[18] The process for preparing a 2,2,6,6-tetramethyl-3,5-heptanedione metal complex according to the process as described in [15], wherein the metal of the metal salt is at least one metal selected from transition metals and alkaline earth metals.

[19] The process for preparing a 2,2,6,6-tetramethyl-3,5-heptanedione metal complex according to the process as described in [18], wherein the metal is at least one metal selected from alkaline earth metals, rare earth metals, Ti, Zr, Hf and Cu.

[20] The process for preparing a 2,2,6,6-tetramethyl-3,5-heptanedione metal complex according to the process as described in [15], wherein a hydrophilic solvent is used as a solvent in the reaction of the 2,2,6,6-tetramethyl-3,5-heptanedione with the metal salt.

[21] The process for preparing a 2,2,6,6-tetramethyl-3,5-heptanedione metal complex according to the process as described in [20], wherein the hydrophilic solvent is an alcohol of 1 to 4 carbon atoms.

[22] The process for preparing a 2,2,6,6-tetramethyl-3,5-heptanedione metal complex according to the process as described in [21], wherein the alcohol is methanol.

[23] The process for preparing a 2,2,6,6-tetramethyl-3,5-heptanedione metal complex according to the process as described in [15], wherein after the reaction is completed, water is added to precipitate the 2,2,6,6-tetramethyl-3,5-heptanedione metal complex, followed by isolating the metal complex.

[24] The process for preparing a 2,2,6,6-tetramethyl-3,5-heptanedione metal complex according to the process described in [15], wherein the 2,2,6,6-tetramethyl-3,5-heptanedione metal complex is a metal complex wherein 2 to 4 molecules of 2,2,6,6-tetramethyl-3,5-heptanedione are coordinated to 1 atom of the metal.

DETAILED DESCRIPTION OF THE INVENTION

The present invention is described in detail hereinafter.

One of the characteristic features of the present invention is to prepare a β-diketone compound represented by the following formula (3) by reacting an ester compound represented by the following formula (1) with a ketone compound represented by the following formula (2) in the presence of an alkali metal alkoxide catalyst, $$CR^1R^2R^3COOR^4 \tag{1}$$

wherein $R^1$ to $R^3$ are each independently an alkyl group of 1 to 3 carbon atoms, and $R^4$ is an alkyl group, $$CR^5R^6R^7COCH_2R^8 \tag{2}$$

wherein $R^5$ to $R^7$ are each independently an alkyl group of 1 to 3 carbon atoms, and $R^8$ is hydrogen or an alkyl group of 1 to 4 carbon atoms, $$CR^1R^2R^3COCHR^8COCR^5R^6R^7 \tag{3}$$

wherein $R^1$ to $R^3$ and $R^5$ to $R^8$ have the same meanings as defined above.

2,2,6,6-tetramethyl-3,5-heptanedione that is particularly useful is taken as an example of the β-diketone compound to explain the invention in detail as below.

The preferred process of the invention is a process for preparing 2,2,6,6-tetramethyl-3,5-heptanedione from a pivalic acid alkyl ester and pinacolone in an organic solvent using an alkali metal alkoxide catalyst. The pivalic acid alkyl ester for use in the invention has a structure of the formula (1) wherein $R^1$ to $R^3$ are each a methyl group and $R^4$ that is an alcohol portion of the ester is not specifically restricted provided that it is an alkyl group. $R^4$ is preferably an alkyl group of 1 to 6 carbon atoms. Examples of such pivalic acid alkyl esters include methyl pivalate, ethyl pivalate, isopropyl pivalate and butyl pivalate.

When $R^4$ is a phenyl group, the reactivity of the ester is per se enhanced, but since the acidity of the phenol liberated is strong, the phenol reacts with the catalyst to form an alkali metal phenoxide that is low-alkaline, and as a result, the reaction is markedly inhibited.

The pinacolone that is a starting material is not specifically restricted, and any of commercially available ones is employable.

In the reaction of the invention, the reactivity greatly varies depending upon the solvent used, and in the beginning of the reaction, the pivalic acid alkyl ester can be used as a solvent by the use of the pivalic acid alkyl ester in a large amount without using any other solvent particularly.

When a solvent other than the pivalic acid alkyl ester is used, an amide type solvent or a urea type solvent is preferably used because the reaction is promoted. The amide type solvent is a compound, which is liquid under the reaction conditions and has an amide bond, such as N,N-dimethylformamide (DMF), N,N-dimethylacetamide (DMAc) or N-methyl-2-pyrrolidone (NMP). The urea type solvent is a compound, which is liquid under the reaction conditions and has a urea bond, such as 1,3-dimethyl-2-imidazolidinone (DMI). Particularly, DMF and DMI are preferable because hydrogen is not present at the α-position to the carbonyl group and any carboanion is not generated, and therefore side reaction due to the condensation reaction of carboanion with ketone or ester can be inhibited. These solvents can be used singly or as a mixture of two or more kinds. It is possible to use other solvents in combination as far as no evil influence is exerted on the reaction (for example, solvents which act on or react with the alkali metal alkoxide catalyst cannot be used). However, if only a solvent other than the amide type or urea type solvent is used, the reactivity is markedly lowered. If the solvent used contains water, the reaction is inhibited, so that it is desirable to dehydrate the solvent prior to use.

The lower limit of the amount of the pivalic acid alkyl ester used as the solvent or the amount of the amide type or urea type solvent is not specifically restricted as far as stirring of the reaction system is feasible. Although the upper limit thereof is not specifically restricted, too dilute reaction system lowers productivity or reactivity and is unfavorable. Therefore, the solvent is preferably used, on the basis of mass, in an amount of 0 to 50 times by mass based on the pinacolone. The amount of the solvent is in the range of more preferably 1 to 40 times by mass, particularly preferably 3 to 30 times by mass. On the basis of mol, the solvent is preferably used in an amount of 0 to 70 times by mol based on the pinacolone. The amount of the solvent is in the range of more preferably 0.2 to 50 times by mol, particularly preferably 0.5 to 20 times by mol.

The amount of the pivalic acid alkyl ester used for the reaction is in the range of 0.5 to 10 times by mol, preferably 1 to 5 times by mol, more preferably 1.1 to 3 times by mol, based on the pinacolone. If the amount of the pinacolone based on the pivalic acid alkyl ester is too large, the yield is lowered by the great influence of self-condensation of the pinacolone. If the amount of the pivalic acid alkyl ester based on the pinacolone is too large, a large amount of the unreacted pivalic acid alkyl ester must be recovered. However, when the pivalic acid alkyl ester is used as the solvent, the pivalic acid alkyl ester used as the starting material and the pivalic acid alkyl ester used as the solvent are not differentiated in the reaction system, so that the pivalic acid alkyl ester is used in an amount of 10 to 30 times by mass based on the pinacolone.

There is no specific limitation on the method of addition of the pivalic acid alkyl ester and the pinacolone, and it is possible to feed the pinacolone previously and then add the pivalic acid alkyl ester slowly or to add the pivalic acid alkyl ester and the pinacolone at the same time. However, in order to prevent self-condensation of the pinacolone, it is preferable to feed the pivalic acid alkyl ester previously and then add the pinacolone slowly so that the amount of the pivalic acid alkyl ester should exceed the amount of the pinacolone in the reaction solution. The pivalic acid alkyl ester and the pinacolone may be added as they are, or they may be added after dissolved in the solvent used.

The reaction temperature is desired to be in the range of 0 to 150° C., preferably 20 to 100° C. If the reaction temperature is too low, the reactivity becomes worse and the reaction time is prolonged, resulting in low productivity. If the reaction temperature is too high, the yield is lowered by the influences of decomposition of the solvent due to alkali and progress of side reaction.

As the alkali metal alkoxide catalyst for use in the reaction, any compound is employable, but the alkali metal is preferably sodium or potassium, more preferably potassium. As the alcohol for forming the alkoxide, a monohydric alcohol having an alkyl group of 1 to 6 carbon atoms which may be branched is usually used, but a polyhydric alcohol (e.g., ethylene glycol or propylene glycol) or an alkoxy alcohol wherein a part of the carbon chain of the alkyl group is replaced with oxygen (e.g., monoalkyl ether of ethylene glycol) may be used. Preferable is a tertiary alcohol having an alkyl group. For example, tert-butoxypotassium can be mentioned.

The alkali metal alkoxide catalysts mentioned above may be used singly or in combination of two or more kinds in an arbitrary proportion. If the amount of the base added is too small, the reactivity becomes worse. If the amount thereof is too large, the yield is lowered by decomposition of the solvent due to alkali or side reaction. The amount of the base is preferably in the range of 1 to 10 mol based on 1 mol of the pinacolone.

When Claisen condensation reaction of the pivalic acid alkyl ester with the pinacolone is carried out in the presence of the alkali metal alkoxide catalyst to synthesize 2,2,6,6-tetramethyl-3,5-heptanedione, the resulting 2,2,6,6-tetramethyl-3,5-heptanedione is present as an alkyl metal salt. In order to isolate the 2,2,6,6-tetramethyl-3,5-heptanedione, the alkali metal salt of 2,2,6,6-tetramethyl-3,5-heptanedione is neutralized with an acid and thereby freed.

Examples of the acids used herein include mineral acids, such as hydrochloric acid, sulfuric acid, nitric acid and phosphoric acid; organic acids, such as formic acid and acetic acid; and Lewis acids, such as ferrous chloride, ferric chloride, stannous chloride and aluminum chloride. Preferably used are sulfuric acid, hydrochloric acid and nitric acid. These acid components may be used singly or in combination of two or more kinds in an arbitrary proportion. The amount of the acid added is sufficient to be not less than the equivalent amount of the alkali metal alkoxide catalyst used for the reaction. Since heat generation takes place in the neutralization, cooling may be carried out if necessary.

In order to recover the 2,2,6,6-tetramethyl-3,5-heptanedione formed by the reaction, water is added to the reaction solution to separate the solution into an oil layer consisting of the 2,2,6,6-tetramethyl-3,5-heptanedione formed by the reaction, a pivalic acid alkyl ester, pinacolone and a solvent, and an aqueous layer consisting of water, a solvent and an inorganic salt. Since the 2,2,6,6-tetramethyl-3,5-heptanedione has bulky hydrophobic groups, it is hardly dissolved in water, so that the 2,2,6,6-tetramethyl-3,5-heptanedione can be recovered in a good recovery ratio even if no extraction agent is used. However, hydrocarbon, ether, aromatic hydrocarbon or the like may be added for the extraction when needed.

The oil layer separated as above can be subjected to distillation purification when needed. The pivalic acid alkyl ester, pinacolone and the solvent having a lower boiling point than the aimed product can be readily recovered and reused for the reaction.

There is no specific limitation on the process to prepare a metal complex from the 2,2,6,6-tetramethyl-3,5-heptanedione prepared by the process of the invention. For example, the metal complex can be prepared by the processes described in Inorganic Synthesis, 11 (1968) and Inorganic Synthesis, 31 (1997). Usually, the metal complex can be prepared by reacting the 2,2,6,6-tetramethyl-3,5-heptanedione with a metal salt in an organic solvent.

The metal of the 2,2,6,6-tetramethyl-3,5-heptanedione metal complex is not specifically restricted provided that it is a metal capable of forming a metal complex together with β-diketone. Preferred examples of such metals include alkaline earth metals, rare earth metals, Ti, Zr, Hf and Cu. Examples of the alkaline earth metals include Sr and Ba, and examples of the rare earth metals include Y, La, Pr, Nd, Sm, Eu, Tm and Tb.

The metal is preferably a metal being divalent to tetravalent ions in consideration of the number being molecules of the 2,2,6,6-tetramethyl-3,5-heptanedione readily coordinated. When the metal ion is n-valent, n molecules of the 2,2,6,6-tetramethyl-3,5-heptanedione are usually coordinated to one metal.

Although the metal salt used for the reaction with the 2,2,6,6-tetramethyl-3,5-heptanedione is not specifically restricted, preferable is a salt of inorganic ion. Examples of such salts include halide, nitrate, sulfate, phosphate and perchlorate. Particularly preferable are nitrate and chloride. These salts may be used singly or as a mixture.

The quantity ratio between the metal salt and the 2,2,6,6-tetramethyl-3,5-heptanedione varies depending upon the valence of the metal of the metal salt, but when the valence of the metal is n, it is preferable to use the 2,2,6,6-tetramethyl-3,5-heptanedione in an amount of n×0.9 to n×1.5 times by mol.

As the solvent for the reaction of the 2,2,6,6-tetramethyl-3,5-heptanedione with the metal salt, an organic solvent can be used without any restriction. The solvent is preferably a solvent capable of dissolving the metal salt. Therefore, preferable is a polar solvent, particularly a hydrophilic solvent, and more preferable is an alcohol type solvent having 1 to 4 carbon atoms. Examples of such solvents include methanol, ethanol, propanol, isopropanol, butanol, methoxyethanol and ethoxyethanol.

The reaction temperature is not lower than the melting point of the solvent and not higher than the boiling point thereof. When the reaction is carried out at a temperature in the vicinity of room temperature, any trouble is not brought about. Accordingly, the reaction temperature is in the range of preferably 10 to 40° C., particularly preferably 15 to 30° C.

When the solvent is hydrophobic, the 2,2,6,6-tetramethyl-3,5-heptanedione metal complex formed by the reaction can be obtained by concentration. When the solvent is a hydrophilic solvent that is usually used, water is added to precipitate the metal complex as solids, and the solids can be isolated by filtration, centrifugation or the like. Depending upon the type of the metal, the metal complex is sometimes precipitated even if water is not particularly added.

The 2,2,6,6-tetramethyl-3,5-heptanedione metal complex can be converted into a metal oxide by the chemical vapor deposition publicly known (e.g., the 4th edition Experimental Chemistry Lectures 13, p. 46). For example, the 2,2,6,6-tetramethyl-3,5-heptanedione metal complex is evaporated to give vapor, and the vapor is mixed with a gas containing oxygen and heated to obtain a metal oxide.

A typical example of such process is MOCVD. MOCVD is a general name of technique wherein an organometallic compound used as a starting material is thermally decomposed in the vicinity of a substrate to perform crystal growth, and this technique is now utilized for the formation of oxides such as compound semiconductor, magnetic substance, ferroelectric thin film and high-temperature superconductor crystal. More specifically, the substrate is heated in a vacuum reactor, then to the vicinity of the substrate, an organometallic compound gas and if desired oxygen are fed, and thermal decomposition reaction is conducted on the substrate surface or in the vicinity of the substrate by induction heating due to high-frequency power or plasma generation to form a metal film or an oxide film on the substrate surface.

It is known that the β-diketone metal complex or its derivative is used as the organometallic compound that is a starting material in MOCVD, and the decomposability of the organometallic compound or the evaporation temperature can be controlled by appropriately selecting the hydrocarbon group of the side chain of the β-diketone that is a ligand.

EXAMPLE

The present invention is further described with reference to the following examples, but it should be construed that the invention is in no way limited to those examples.

Quantitative determination of 2,2,6,6-tetramethyl-3,5-heptanedione in the following examples was made by gas chromatography. The analytical conditions are described below. With regard to the 2,2,6,6-tetramethyl-3,5-heptanedione, a reagent having a purity of not less than 95% available from Wako Junyaku K.K. was used as a standard product of 95% purity.

Gas Chromatography Conditions
Apparatus: GC-14A manufactured by Shimadzu Seisakusho K.K., Split method (Split Ratio: 60)
Capillary Column: DB-5 manufactured by J&W Co., 0.25 mmø×30 m, stationary liquid thickness: 0.25μ
Carrier gas: helium
Injection quantity: 1 μl
INJ. temperature: 250° C.
DET. temperature (FID): 280° C.
Temperature program: 50° C.→5 min, hold→10° C./min, heating up to 250° C.
Quantitative determination method: internal standard method (internal standard substance: naphthalene)

Example 1

In a 2-liter four-necked flask, 1000 g of DMF and 135 g of tert-butoxypotassium were placed, and they were heated up to 50° C. with stirring by a mechanical stirrer. Then, 186 g of methyl pivalate was added by a dropping funnel. Thereafter, a mixed solution of 80 g of pinacolone and 100 g of DMF was added by a dropping funnel over a period of 3 hours, followed by further stirring for 5 hours under heating. It was confirmed by gas chromatography that 2,2,6,6-tetramethyl-3,5-heptanedione was produced in an amount of 76.5 g (yield: 52% (based on pinacolone)) in the solution.

Example 2

The reaction was carried out in the same manner as in Example 1, except that the solvent was changed to DMAc. It was confirmed by gas chromatography that 2,2,6,6-tetramethyl-3,5-heptanedione was produced in an amount of 47.1 g (yield: 32% (based on pinacolone)) in the solution.

Example 3

The reaction was carried out in the same manner as in Example 1, except that the solvent was changed to DMI. It was confirmed by gas chromatography that 2,2,6,6-tetramethyl-3,5-heptanedione was produced in an amount of 88.3 g (yield: 60% (based on pinacolone)) in the solution.

Example 4

The reaction was carried out in the same manner as in Example 1, except that the solvent was changed to NMP. It was confirmed by gas chromatography that 2,2,6,6-tetramethyl-3,5-heptanedione was produced in an amount of 58.9 g (yield: 40% (based on pinacolone)) in the solution.

Example 5

The reaction was carried out in the same manner as in Example 1, except that the amount of tert-butoxypotassium was changed to 270 g. It was confirmed by gas chromatography that 2,2,6,6-tetramethyl-3,5-heptanedione was produced in an amount of 103.0 g (yield: 70% (based on pinacolone)) in the solution.

Example 6

The reaction was carried out in the same manner as in Example 1, except that tert-butoxypotassium was replaced with 81.6 g of sodium ethoxide. It was confirmed by gas chromatography that 2,2,6,6-tetramethyl-3,5-heptanedione was produced in an amount of 22.1 g (yield: 15% (based on pinacolone)) in the solution.

Example 7

The reaction was carried out in the same manner as in Example 1, except that tert-butoxypotassium was replaced with 115.2 g of tert-butoxysodium. It was confirmed by gas chromatography that 2,2,6,6-tetramethyl-3,5-heptanedione was produced in an amount of 61.8 g (yield: 42% (based on pinacolone)) in the solution.

Example 8

The reaction was carried out in the same manner as in Example 1, except that the reaction temperature was changed to 90° C. It was confirmed by gas chromatography that 2,2,6,6-tetramethyl-3,5-heptanedione was produced in an amount of 66.2 g (yield: 45% (based on pinacolone)) in the solution.

Example 9

The reaction was carried out in the same manner as in Example 1, except that any particular solvent is not used but methyl pivalate was used in the same amount as that of DMF. It was confirmed by gas chromatography that 2,2,6,6-tetramethyl-3,5-heptanedione was produced in an amount of 44.2 g (yield: 30% (based on pinacolone)) in the solution.

Reference Example 1

The reaction was carried out in the same manner as in Example 1, except that the solvent was changed to 1,4-dioxane. As a result, the yield was 1% (based on pinacolone).

Reference Example 2

The reaction was carried out in the same manner as in Example 1, except that the solvent was changed to acetonitrile. As a result, 2,2,6,6-tetramethyl-3,5-heptanedione was hardly produced.

Reference Example 3

The reaction was carried out in the same manner as in Example 1, except that the solvent was changed to tert-butyl methyl ether. As a result, the yield was 2% (based on pinacolone).

Reference Example 4

The reaction was carried out in the same manner as in Example 1, except that the solvent was changed to toluene. As a result, the yield was 4% (based on pinacolone).

Reference Example 5

The reaction was carried out in the same manner as in Example 1, except that the solvent was changed to tert-butanol. As a result, 2,2,6,6-tetramethyl-3,5-heptanedione was hardly produced.

Reference Example 6

The reaction was carried out in the same manner as in Example 1, except that the solvent was changed to dimethyl sulfoxide. As a result, the yield was 10% (based on pinacolone).

Reference Example 7

The operations of Example 1 were carried out using dichloromethane as a solvent. As a result, heat generation took place in the stage of mixing dichlormethane with tert-butoxypotassium, and the desired reaction did not proceed.

Reference Example 8

The reaction was carried out in the same manner as in Example 7, except that the solvent was changed to xylene. As a result, 2,2,6,6-tetramethyl-3,5-heptanedione was hardly produced.

Comparative Example 1

The reaction was carried out in the same manner as in Example 1, except that methyl pivalate was replaced with phenyl pivalate. As a result, 2,2,6,6-tetramethyl-3,5-heptanedione was not produced.

Example 10

To the reaction solution containing 2,2,6,6-tetramethyl-3,5-heptanedione, said reaction solution having been synthesized in the same manner as in Example 1, 74.3 g of sulfuric acid was added and then 1000 g of water was further added, to separate the solution into two layers of an oil layer and an aqueous layer. The oil layer was recovered and analyzed by GC. As a result, the recovery of 2,2,6,6-tetramethyl-3,5-heptanedione was 99.5%.

Example 11

In 1155 g of methanol, 40.4 g (1.01 mol) of NaOH of 96% purity was dissolved with stirring, and the resulting solution was cooled to room temperature. Then, 180.3 g (0.882 mol) of 2,2,6,6-tetramethyl-3,5-heptanedione of 90% purity was added little by little. To the mixture, a solution obtained by dissolving 132 g (0.294 mol) of $Y(NO_3)_3 \cdot 6H_2O$ of 85.6% purity in 1225 g of methanol was added at a temperature of 25 to 28° C. over a period of 30 minutes. The reaction was conducted for 1 hour, and the crystals precipitated were filtered off. To the resulting solution, 3500 g of water was dropwise added over a period of 1 hour and 30 minutes. After the dropwise addition was completed, stirring was performed for 1 hour. The resulting crystals were taken out by centrifugation and then dried. Thus, 166.8 g (yield: 89%) of tris(2,2,6,6-tetramethyl-3,5-heptanedionato)yttrium was obtained.

Example 12

In 256 g of methanol, 48.6 g (0.252 mol) of a sodium methylate methanol solution of 28% purity was dissolved, and the resulting solution was cooled to room temperature. Then, 49.3 g (0.252 mol) of 2,2,6,6-tetramethyl-3,5-heptanedione of 94% purity was dropwise added with stirring. To the mixture, a solution obtained by dissolving 45.8 g (0.084 mol) of $Eu(NO_3)_3 \cdot 6H_2O$ of 81.9% purity in 367 g of methanol was added at a temperature of 25 to 28° C. over a period of 30 minutes. The reaction was conducted for 1 hour, and the crystals precipitated were filtered off. To the resulting solution, 1000 g of water was dropwise added over a period of 1 hour and 30 minutes. After the dropwise addition was completed, stirring was performed for 1 hour. The resulting crystals were taken out by centrifugation and then dried. Thus, 55.2 g (yield: 93.6%) of tris(2,2,6,6-tetramethyl-3,5-heptanedionato)europium was obtained.

Example 13

55.2 g (yield: 93.6%) of tris(2,2,6,6-tetramethyl-3,5-heptanedionato)terbium was obtained in the same manner as in Example 12, except that 49.3 g (0.252 mol) of 2,2,6,6-tetramethyl-3,5-heptanedione of 94% purity was used as 2,2,6,6-tetramethyl-3,5-heptanedione and 46.0 g (0.084 mol) of $Tb(NO_3)_3 \cdot 6H_2O$ of 82.7% purity was used instead of $Eu(NO_3)_3 \cdot 6H_2O$.

Example 14

To 177 g of methanol, 43.7 g (0.216 mol) of 2,2,6,6-tetramethyl-3,5-heptanedione of 91% purity was dropwise added with stirring. To the resulting solution, a solution, which had been obtained by dissolving 12.7 g (0.054 mol) of $ZrCl_4$ of 99% purity in 218 g of methanol and cooled to room temperature, was added over a period of about 5 minutes. The reaction was conducted for 1 hour with stirring, and 590 g of water was added over a period of 50 minutes. Then, stirring was performed for 1 hour. The resulting solution was adjusted to pH 6.6 with a 20% NaOH solution. The resulting crystals were collected by centrifugation and then dried. Thus, 43.9 g (yield: 98.2%) of tetrakis(2,2,6,6-tetramethyl-3,5-heptanedionato)zirconium was obtained.

Example 15

In 67 g of methanol, 6.6 g (0.0366 mol) of a sodium methylate methanol solution of 30% purity was dissolved, and the resulting solution was cooled to room temperature. Then, 7.41 g (0.0366 mol) of 2,2,6,6-tetramethyl-3,5-heptanedione of 91% purity was dropwise added with stirring. To the mixture, a solution obtained by dissolving 4.83 g (0.0183 mol) of $Ba(NO_3)_2$ of 99% purity in 38 g of water was added. The reaction was conducted for 1 hour, and 100 g of water was dropwise added. After the dropwise addition was completed, stirring was performed for 1 hour. The resulting crystals were taken out by centrifugation and then dried. Thus, 8.07 g (yield: 87.6%) of bis(2,2,6,6-tetramethyl-3,5-heptanedionato)barium was obtained.

Example 16

7.28 g (yield: 87.7%) of bis(2,2,6,6-tetramethyl-3,5-heptanedionato)strontium was obtained in the same manner as in Example 15, except that 3.87 g of $Sr(NO_3)_2$ of 99.5% purity was used instead of $Ba(NO_3)_2$.

Example 17

In 53.2 g of methanol, 9.31 g (0.0517 mol) of a sodium methylate methanol solution of 30% purity was dissolved, and the resulting solution was cooled to room temperature. Then, 10.5 g (0.0517 mol) of 2,2,6,6-tetramethyl-3,5-heptanedione of 91% purity was dropwise added with stirring. Then, 6.46 g (0.0259 mol) of $Cu(NO_3)_2 \cdot 6H_2O$ was added. The reaction was conducted for 1 hour, and the crystals precipitated were collected by filtration. The crystals were dissolved in 100 g of diethyl ether, washed 5 times with 100 g of water and then evaporated to dry. Thus, 8.74 g (yield: 78.7%) of bis(2,2,6,6-tetramethyl-3,5-heptanedionato)copper was obtained.

EFFECT OF THE INVENTION

According to the present invention, it becomes possible to use as a catalyst an alkali metal alkoxide that is easy to handle, and 2,2,6,6-tetramethyl-3,5-heptanedione can be prepared under mild conditions at a low cost without necessity to invest a large sum of money in plant and equipment.

The 2,2,6,6-tetramethyl-3,5-heptanedione prepared by the invention can be coordinated to a metal to synthesize a complex, and hence a 2,2,6,6-tetramethyl-3,5-heptanedione metal complex that is a starting material of MOCVD can be provided at a low cost.

The invention claimed is:

1. A process for preparing a β-diketone compound represented by the following formula (3), comprising reacting an ester compound represented by the following formula (1) with a ketone compound represented by the following formula (2) in the presence of an alkali metal alkoxide catalyst, $$CR^1R^2R^3COOR^4 \quad (1)$$

wherein $R^1$ to $R^3$ are each independently an alkyl group of 1 to 3 carbon atoms, and $R^4$ is an alkyl group, $$CR^5R^6R^7COCH_2R^8 \quad (2)$$

wherein $R^5$ to $R^7$ are each independently an alkyl group of 1 to 3 carbon atoms, and $R^8$ is hydrogen or an alkyl group of 1 to 4 carbon atoms, $$CR^1R^2R^3COCHR^8COCR^5R^6R^7 \quad (3)$$

wherein $R^1$ to $R^3$ and $R^5$ to $R^8$ have the same meanings as defined above, and wherein a solvent is used in the process, and the solvent is an amide type solvent, a urea type solvent or a mixture thereof.

2. The process for preparing a β-diketone compound as claimed in claim 1, wherein at least one compound selected from an ester compound represented by the following formula (1), an amide type solvent and a urea type solvent is used as a solvent, $$CR^1R^2R^3COOR^4 \quad (1)$$

wherein $R^1$ to $R^3$ are each independently an alkyl group of 1 to 3 carbon atoms, and $R^4$ is an alkyl group.

3. The process for preparing a β-diketone compound as claimed in claim 1, wherein the compound represented by the formula (1) is a pivalic acid alkyl ester wherein $R^1$ to $R^3$ are each a methyl group, the compound represented by the formula (2) is pinacolone wherein $R^5$ to $R^7$ are each a methyl group and $R^8$ is hydrogen, and the compound represented by the formula (3) is 2,2,6,6-tetramethyl-3,5-heptanedione wherein $R^1$ to $R^3$ and $R^5$ to $R^7$ are each a methyl group and $R^8$ is hydrogen.

4. The process for preparing a β-diketone compound as claimed in claim 3, wherein the reaction is carried out using a pivalic acid alkyl ester as a solvent and using no other solvent.

5. The process for preparing a β-diketone compound as claimed in claim 3, wherein an amide type solvent or a urea type solvent is used as a solvent.

6. The process for preparing a β-diketone compound as claimed in claim 5, wherein the solvent is at least one solvent selected from N,N-dimethylformamide, N,N-dimethylacetamide, N-methylpyrrolidone and 1,3-dimethyl-2-imidazolidinone.

7. The process for preparing a β-diketone compound as claimed in claim 6, wherein the solvent is N,N-dimethylformamide and/or 1,3-dimethyl-2-imidazolidinone.

8. The process for preparing a β-diketone compound as claimed in claim 4, wherein the amount of the solvent used is in the range of 3 to 30 times by mass based on the pinacolone.

9. The process for preparing a β-diketone compound as claimed in claim 3, wherein the alkali metal of the alkali metal alkoxide catalyst is sodium or potassium.

10. The process for preparing a β-diketone compound as claimed in claim 9, wherein the alcohol portion of the alkali metal alkoxide catalyst is a tertiary alcohol.

11. The process for preparing a β-diketone compound as claimed in claim 3, wherein the amount of the alkali metal alkoxide catalyst used is in the range of 1 to 10 times by mol based on the pinacolone.

12. A process for preparing 2,2,6,6-tetramethyl-3,5-heptanedione, comprising carrying out the process in any one of claims 3 to 11 to synthesize 2,2,6,6-tetramethyl-3,5-heptanedione by reacting the pivalic acid alkyl ester with the pinacolone in the presence of the alkali metal alkoxide catalyst and adding an acid to the reaction solution of 2,2,6,6-tetramethyl-3,5-heptanedione to perform neutralization and adding water to the solution to separate the solution into two layers and thereby isolate the 2,2,6,6-tetramethyl-3,5-heptanedione as an oil layer.

13. The process for preparing 2,2,6,6-tetramethyl-3,5-heptanedione as claimed in claim 12, wherein the acid is at least one acid selected from sulfuric acid, hydrochloric acid and nitric acid.

14. A process for preparing 2,2,6,6-tetramethyl-3,5-heptanedione, comprising recovering a pivalic acid alkyl ester, pinacolone and a solvent from the oil layer containing 2,2,6,6-tetramethyl-3,5-heptanedione obtained in the process of claim 12 by distillation separation and reusing them in the reaction.

15. A process for preparing a 2,2,6,6-tetramethyl-3,5-heptanedione metal complex, comprising carrying out a reaction to obtain 2,2,6,6-tetramethyl-3,5-heptanedione in the process as claimed in claim 3 and reacting the thus-obtained 2,2,6,6-tetramethyl-3,5-heptanedione with a metal salt.

16. The process for preparing a 2,2,6,6-tetramethyl-3,5-heptanedione metal complex as claimed in claim 15, wherein the metal salt is at least one metal salt selected from the group consisting of a halide, a nitrate, a sulfate and a phosphate of a metal.

17. The process for preparing a 2,2,6,6-tetramethyl-3,5-heptanedione metal complex as claimed in claim 16, wherein the metal salt is a chloride of a metal and/or a nitrate of a metal.

18. The process for preparing a 2,2,6,6-tetramethyl-3,5-heptanedione metal complex as claimed in claim 15, wherein the metal of the metal salt is at least one metal selected from transition metals and alkaline earth metals.

19. The process for preparing a 2,2,6,6-tetramethyl-3,5-heptanedione metal complex as claimed in claim 18, wherein the metal is at least one metal selected from alkaline earth metals, rare earth metals, Ti, Zr, Hf and Cu.

20. The process for preparing a 2,2,6,6-tetramethyl-3,5-heptanedione metal complex as claimed in claim 15, wherein a hydrophilic solvent is used as a solvent in the reaction of the 2,2,6,6-tetramethyl-3,5-heptanedione with the metal salt.

21. The process for preparing a 2,2,6,6-tetramethyl-3,5-heptanedione metal complex as claimed in claim 20, wherein the hydrophilic solvent is an alcohol of 1 to 4 carbon atoms.

22. The process for preparing a 2,2,6,6-tetramethyl-3,5-heptanedione metal complex as claimed in claim 21, wherein the alcohol is methanol.

23. The process for preparing a 2,2,6,6-tetramethyl-3,5-heptanedione metal complex as claimed in claim 15, wherein after the reaction is completed, water is added to precipitate the 2,2,6,6-tetramethyl-3,5-heptanedione metal complex, followed by isolating the metal complex.

24. The process for preparing a 2,2,6,6-tetramethyl-3,5-heptanedione metal complex as claimed in claim 15, wherein the 2,2,6,6-tetramethyl-3,5-heptanedione metal complex is a metal complex wherein 2 to 4 molecules of 2,2,6,6-tetramethyl-3,5-heptanedione are coordinated to 1 atom of the metal.

25. The process for preparing a β-diketone compound as claimed in claim 1, wherein the solvent is an amide type solvent that has no hydrogen at the α-position to a carbonyl group, a urea type solvent that has no hydrogen at the α-position to a carbonyl group or a mixture thereof.

26. The process for preparing a β-diketone compound as claimed in claim 1, wherein the solvent is a urea type solvent or an amide type solvent selected from the group consisting of N,N-dimethylformamide, N,N-dimethylacetamide and 1,3-dimethyl-2-imidazolidinone.

27. The process for preparing a β-diketone compound as claimed in claim 1, wherein the alkali metal alkoxide catalyst is a tert-butoxide of sodium or potassium.

* * * * *